United States Patent
Jalk et al.

(10) Patent No.: US 7,639,150 B2
(45) Date of Patent: Dec. 29, 2009

(54) METHOD AND A DEVICE FOR DETECTING SLAG

(75) Inventors: Mats Jalk, Nyköping (SE); Willy Ohlsson, Nyköping (SE); Håkan Kelvesjö, Nyköping (SE)

(73) Assignee: MPC Metal Process Control AG, Nyköping (SE)

( * ) Notice: Subject to any disclaimer, the term of this patent is extended or adjusted under 35 U.S.C. 154(b) by 704 days.

(21) Appl. No.: 10/560,600

(22) PCT Filed: Apr. 23, 2004

(86) PCT No.: PCT/EP2004/004314
§ 371 (c)(1),
(2), (4) Date: Jun. 12, 2006

(87) PCT Pub. No.: WO2004/110675
PCT Pub. Date: Dec. 23, 2004

(65) Prior Publication Data
US 2006/0266796 A1    Nov. 30, 2006

(30) Foreign Application Priority Data
Jun. 13, 2003  (EP) .................................. 03013294

(51) Int. Cl.
*G08B 21/00* (2006.01)
(52) U.S. Cl. ........................ 340/603; 340/606; 75/10.12
(58) Field of Classification Search .................. 340/603, 340/606, 610, 612, 613, 617; 75/10.12, 10.24, 75/10.61; 164/453, 465, 504, 154.1
See application file for complete search history.

(56) References Cited

U.S. PATENT DOCUMENTS

| | | | |
|---|---|---|---|
| 4,144,756 A | | 3/1979 | Linder |
| 4,816,758 A | | 3/1989 | Theissen et al. |
| 5,429,655 A | * | 7/1995 | Ogura et al. ................ 75/10.61 |
| 5,746,268 A | * | 5/1998 | Fujisaki et al. ............... 164/468 |
| 6,019,811 A | * | 2/2000 | Schlienger et al. .......... 75/10.12 |
| 7,013,949 B2 | * | 3/2006 | Cervantes et al. ............ 164/453 |

FOREIGN PATENT DOCUMENTS

| | | |
|---|---|---|
| JP | 54-110932 A | 8/1979 |
| JP | 54-119336 A | 9/1979 |
| JP | 9-236461 A | 9/1997 |
| JP | 10-5958 A | 1/1998 |
| WO | WO 02/36293 A | 5/2002 |

OTHER PUBLICATIONS

International Search Report, Jul. 12, 2004.
International Preliminary Examination Report issued on Dec. 13, 2005.

* cited by examiner

*Primary Examiner*—Van T. Trieu
(74) *Attorney, Agent, or Firm*—Harness, Dickey & Pierce, P.L.C.

(57) ABSTRACT

A method and device are provided for detecting the presence of slag in a shroud through which molten metal passed from a ladle to a tundish. An induced voltage generated at a receiving coil is compared with a defined voltage range. If the induced voltage has a value outside the defined voltage range, it is indicative of the presence of slag. The voltage range is defined in dependence of the flow of molten metal passing through the shroud. A casting plant is also provided.

27 Claims, 3 Drawing Sheets

METHOD AND A DEVICE FOR DETECTING SLAG

TECHNICAL FIELD OF THE INVENTION

The present invention relates to a method and a device for detecting slag. In particular, the invention relates to detecting the presence of slag in a shroud which guides molten metal from a ladle to a tundish. The invention also relates to a casting plant comprising such a device.

BACKGROUND OF THE INVENTION

In the metallurgical industry there are different processes in which liquid metal is to be processed in one way or another. One example is the casting of metal, such as steel. In part of such a casting process, the liquid metal is supplied from a ladle to a tundish via a pouring nozzle which is generally referred to as a shroud. The metal flows from the tundish via another pouring nozzle to a casting mould or chill mould, in which the metal is cooled and transformed into solid form.

In smelting and heating processes there is a risk of slag being formed in the molten metal. In order to minimize the risk of slag being included in the final cast product, the casting plant may include a slag detection device. If the slag detection device detects slag in the molten metal an alarm is generated so that suitable measures may be taken.

In the prior art one type of slag detection device includes electromagnetic coils placed above a sliding gate in the ladle. This type of slag detection device works on the principle that for an electromagnetic field the penetration depth of metal is much less than the penetration depth of slag. Thus, a large portion of the electromagnetic field is allowed to pass through slag, similarly to air, and therefore it may be difficult for the device to distinguish slag from gas (such as air). In the bottom of the ladle, i.e. just above the sliding gate, this is not a significant problem since at the measuring area of the ladle it is generally filled with molten metal.

However, it would also be desirable to detect slag in the shroud between the ladle and the tundish, This would avoid the necessity of installing slag detecting electromagnetic sensors (coils) in every ladle used in a casting plant. Furthermore, sensors installed in a ladle are in such a position where there is a relatively high risk of mechanically damaging the sensors. Thus, it would be desirable to install electromagnetic slag detecting sensors in such manner that cut costs and minimizes the risk of mechanical damage to the sensors. Even though there exists slag detecting devices that comprise vibration meters or vibration meters combined with infrared measuring devices, there still lacks a satisfactory method of detecting slag in the shroud by means of electromagnetism. The reason for this is that the molten metal passing from the ladle through the shroud does not always completely fill the shroud. Consequently, the portion of the shroud which contains gas instead of metal may be mistaken for slag, resulting in the generation of a false alarm.

SUMMARY OF THE INVENTION

An object of the present invention is to achieve a method, a device and a casting plant which are suitable for detecting slag in a shroud extending between a ladle and a tundish.

This and other objects, which will become apparent in the following, are accomplished by a method, a device and a casting plant as defined in the accompanied claims.

According to one aspect of the invention, there is provided a method of detecting the presence of slag in a shroud for guiding molten metal from a ladle to a tundish. According to this method a transmitting coil is used for generating an electromagnetic field which enters the shroud and its contents. A receiving coil is used to receive the electromagnetic field that has entered the shroud. The electromagnetic field generates an induced voltage in the receiving coil. If the value of the induced voltage is outside a defined voltage range, it is indicative of the presence of slag in said contents. Said voltage range is defined depending on the magnitude of the flow of molten metal passing through the shroud. Said magnitude may be determined either directly at the shroud or indirectly by measuring at another location and from the measurement calculating the flow inside the shroud.

According to a second aspect of the invention, there is provided a device for detecting slag in line with the above mentioned method.

Thus, the invention is based on the insight that slag may successfully be detected also in spaces, such as shrouds, which are not necessarily completely filled with molten metal, by setting an alarm limit depending on the amount of gas (e.g. air) present. In particular, the invention is based on the insight that the presence of gas can be determined by determining the flow, i.e. the volume per unit of time, of molten metal passing through the shroud.

The advantage of determining the flow of molten metal is that it provides a ratio of the flow components, i.e. the amount of metal to the amount of gas in the shroud, wherein depending on a change in said ratio the sensitivity of the detection device may be varied. For instance, if the flow of molten metal decreases after a while, the requirement for or level of providing an alarm of the detection device is increased. This is done by increasing said defined voltage range. This means that a given induced voltage may be either indicative of the presence of slag or not depending on the presently defined voltage range. Thus, on the one hand a given induced voltage value may fall outside a voltage range defined before a decrease of the flow, which would result in an indication of presence of slag and on the other hand, after the decrease of the flow and the increase of the voltage range, the same value of induced voltage would be covered by the redefined voltage range, wherein it would be construed as presence of gas, if any, and not slag. The risk of slag being entrained in the flow of molten metal usually increases towards the end of the process, when the ladle is close to being drained.

The variation of voltage range may be illustrated in the following way. Suppose that the receiving coil, for an empty shroud, i.e. just gas and no molten metal, generates an induced voltage having a signal strength $V_1$. When molten metal passing through the shroud completely fills up the shroud a voltage having a signal strength $V_2$ will be induced, wherein $V_2<V_1$. Thus, for a filled shroud the voltage range is set to at least the interval $0-V_2$, however, in order to be on the safe side and not risk a false alarm, the voltage range may be extended somewhat. When the shroud is only partly filled with molten metal, the definition of the voltage range is suitably adjusted. The newly defined voltage range will be $0-V_3$, wherein $V_2<V_3<V_1$.

A simple calculation example will now follow.

Suppose that for a shroud completely filled with molten metal the voltage range is defined such that the slag is only indicated as being present if the magnitude of the induced voltage indicates a metal content of 90% or less (while the determined magnitude of flow of molten metal is still about 100%). Thus, if the induced voltage corresponds to a shroud filled by 95% with molten metal, there will be no slag indication. This provides a 10% safety margin for avoiding false alarm. Now, suppose that later on it is determined that the flow of molten metal has decreased to half, i.e. only 50% of the shroud is filled with molten metal and the rest is filled with gas. In order to maintain the 10% safety margin the voltage range is defined such that the presence of slag is indicated if the value of the induced voltage corresponds to a metal content of 45% or less. Note that the numbers in the this example are merely exemplifying in order to illustrate a general principle of varying the voltage range.

As previously mentioned, the flow of molten metal guided through the shroud may be determined either directly or indirectly. Different types of flow meters may be employed for direct measurement of the flow inside the shroud. However, it may be simpler to make use of an indirect method of determination. For instance, the flow of molten metal passing through the shroud may be determined by measuring the teeming rate in the tundish and calculating the flow of molten metal from said measured teeming rate. Another alternative is to measure the rate of decrease in weight of the ladle content and calculating the flow of molten metal from said measured rate of decrease in weight. Yet another alternative is to measure the casting speed and the dimension of the cast product after the chill mould, the speed and dimension being indicative of the flow. A further alternative is to detect the degree of opening or the position of the sliding gate mounted under the ladle and to provide a feedback signal to a processor, which calculates the flow of molten metal from the positional information of the sliding gate, i.e. how much the siding gate has been opened. An advantage of these different alternatives is that standard existing measuring systems may be used to provide the relevant information desired to define slag alarm settings.

The transmitting coil and the receiving coil are suitably held in place by either a common or separate coil holders. If a common coil holder is to be utilised it may be designed in the form of a fork having at least two branches. The transmitting coil and the receiving coil may then be held by respective branches adapted to be placed on respective sides of the shroud. The forked coil holder may either stand by itself or be connected to other equipments as will be explained below.

During the process of slag detection the coils are preferably kept substantially unmovable relative to the shroud. If the coils are unmovable relative to the shroud, i.e. they follow any movement of the shroud, an even signal is obtained for an unchanged flow of molten metal. This may be accomplished by e.g. mounting the transmitting coil and the receiving coil to respective branches of a forked coil holder mentioned above. In that case, the forked coil holder is suitably placed in such manner that an imagined straight line drawn between the transmitting coil and the receiving coil crosses the shroud. In other words the shroud is placed between the branches of the forked coil holder. An advantage of using a forked coil holder is that it is possible to use a relatively long stem thereof, wherein positioning of the coils around the shroud can be accomplished by maneuverings at a distance from the shroud without having to access the shroud closely. The branches of the forked coil holder facilitate correct positioning of the coils and reduces the risk of relative movements between the coils thereby avoiding unnecessary erroneous signal variations. The risk of relative movements between the coils are further reduced if the branches are made relatively short. Thus, a relatively long stem having short branches may suitably be used. Since the forked coil holder, preferably, does not entirely surround the circumference of the shroud it is easily locatable to and removable from the shroud.

In order to enable the coils to substantially follow any movement of the shroud, the forked coil holder is suitably suspended to an arrangement that follows the movements of the shroud. One example of such an arrangement is a shroud manipulator of any known type. A shroud manipulator is generally in the form of an elongate arm that is used to fetch, position and support the shroud. The forked coil holder may thus be mounted to such a shroud manipulator. As an alternative, the forked coil holder may be suspended to the sliding gate unit mounted on the ladle, and other alternatives are also possible in order to achieve the desired motion following effect.

The two branches that hold the transmitting coil and the receiving coil respectively may in at least one embodiment of the invention be electrically isolated from one another. If for example the branches are connected to the stem by means of a common cross bar, that bar may be provided with electrical isolation. This type of interruption minimizes unwanted electromagnetic fields.

Even though the forked coil holder provides many advantages, the method according to the present invention, could also be carried out by arranging the coils on separate holding elements, e.g. separate arms, that are electrically isolated from one another. Such separate holding elements may also be mounted to the shroud manipulator or other shroud motion following arrangement. Accordingly, there are different ways in which to generate an electromagnetic field by means of one or more transmitting coils from one side of the shroud and to receive said electromagnetic field by means of one or more receiving coils on another side of the shroud.

According to at least one embodiment of the invention, as an alternative to providing transmitting and receiving coils on different sides of the shroud, each coil is arranged to surround the shroud. The coils may be given a toroid or annular form and the shroud will extend through each toroid. The coils may be mounted to the shroud by means of a coil holder arrangement including fasteners for securing the coils to the shroud. Alternatively, the annular configuration can be mounted to some other location, such as the sliding gate at the ladle, and be suspended therefrom so as to surround the shroud. Another alternative is to mount the coils between the branches of a forked coil holder which in turn is mounted to a shroud manipulator or other shroud following arrangement.

It should be clear from the above discussion that regardless of the type of coil arrangement chosen, it is possible to arrange the coils in such manner that the coils are enabled to substantially follow any positional variations of the shroud. The advantage of this is that the propagation of the generated magnetic field entering the shroud will be constant, wherein the accuracy of the detection is increased. Movement of the shroud may occur during the pouring of the molten metal. Such movement may be linear or in arcs of a circle. The shroud also tends to move when the sliding gate at the ladle is moved.

In at least one embodiment of the invention, as a supplement to the control of the defined voltage range, the frequency of the electromagnetic field generated by the transmitting coil may be controlled. It has been found that a higher frequency provides a more stable induced voltage signal when the shroud is not completely filled and a turbulent flow of molten metal is present inside the shroud. Thus, when a turbulent flow inside the shroud has been detected, the frequency of the electromagnetic field is changed, suitably increased, by the system. Also, the magnitude of the flow of molten metal influences the chosen frequency in order to penetrate the metal and detect any slag in the centre of or at any other place if the flow of molten metal. External frequencies that can interfere with the measurement can be a ground for changing the frequency. Thus, the electromagnetic field generated by the transmitting coils(s) may be of alternating frequencies.

Also, several coils may be used for generating several electromagnetic fields, each with a different frequency, in order to minimise noise effects. Furthermore, several coils may be used for generating several electromagnetic fields, one or more being of alternating frequencies.

The transmitting coil that generates the electromagnetic field may be provided with directional elements, such as a core, for optimised direction of the electromagnetic field towards the portion of the shroud in which it is intended to check whether or not slag is present. Similarly the receiving coil may be provided with such directional elements.

Due to the high temperature environment, according to at least one embodiment of the invention, the transmitting and receiving coils may be cooled by means of a suitable cooling arrangement, such as cooling channels containing water or gas.

According to a third aspect of the invention, there is provided a device for detecting the presence of slag in a shroud which guides molten metal from a ladle to a tundish, the device comprising a forked coil holder having at least two branches, a first branch carrying a transmitting coil and a second branch carrying a receiving coil, the two branches being placeable in such manner that the shroud is located between them. This enables the coils to be substantially unmovable relative to each other and the shroud and the contained metal stream, thereby avoiding unwanted signal variations. Another advantage is that the coils are independent of the ladle.

According to a fourth aspect of the invention, there is provided a casting plant, which comprises a ladle, a tundish and a shroud between them. The casting plant also comprises a device for detecting the presence of slag inside the shroud, as has been previously described in this application.

BRIEF DESCRIPTION OF THE DRAWINGS

The invention will now be described with reference to the accompanied drawings, in which.

DETAILED DESCRIPTION OF THE DRAWINGS

Figure 1:
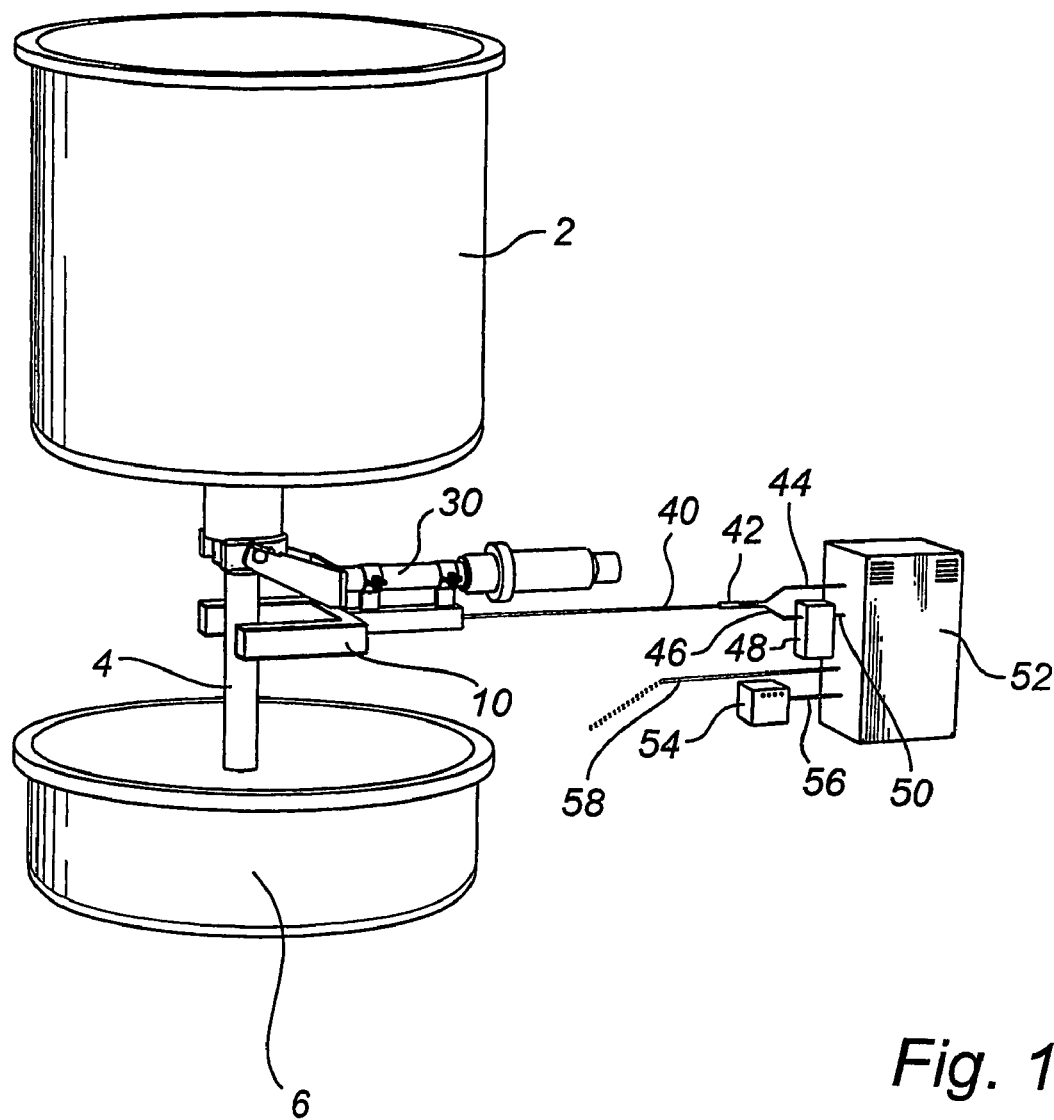
FIG. 1 is a schematic illustration of a device arranged to detect slag in a shroud in accordance with at least one embodiment of the invention.

FIG. 1 schematically illustrates a ladle 2 adapted to contain molten metal which is to be passed through a shroud 4 over to a tundish 6. The metal flows from the tundish 6 via a pouring nozzle to a chill mould, in which the metal is cooled and transformed into solid form, the pouring nozzle and the chill mould not being shown in the figure. A forked coil holder 10 is provided at the outside of the shroud 4 and is mounted to a shroud manipulator 30. The forked coil holder 10 contains a transmitting coil for generating an electromagnetic field to be propagated through the shroud and to be received by a receiving coil which is also located in the forked coil holder 10. The forked coil holder 10 and the coils will be further described in connection with the discussion of FIG. 2.

Continuing with FIG. 1, a signal cable 40 extends between the forked coil holder 10 and a connector 42. The signal cable 40 contains internal cables or separate wires for leading signals to and from the transmitting coil and the receiving coil, respectively. Also connected to the connector 42 are a transmitter signal cable 44 and a receiver signal cable 46 containing wires for providing signals to and from the transmitting coil and the receiving coil, respectively. The receiver signal cable 46 is at its other end connected to a preamplifier unit 48 in order to amplify generated induced voltage signals from the receiving coil. A preamplifier cable 50 passes on the signals to a control unit 52 which comprises a processor. The transmitter signal cable 44 is directly connected to the control unit 52. The generation of an electromagnetic field by the transmitting coil can thus be controlled by sending a signal from the control unit 52, via the transmitter signal cable 44, the connector 42 and the associated wires in the signal cable 40 to the transmitting coil inside the forked coil holder 10.

The control unit 52 is connected to an alarm unit 54 via an alarm cable 56. The control unit 52 compares the received induced voltage signal from the receiving coil with a predefined voltage range. If the received voltage is not included in said voltage range, the control unit 52 activates the alarm unit 54, which may suitably generate an acoustic and/or visual alarm. Also, even though not shown, a control panel may be provided for enabling continuous visual monitoring of the slag detection process.

Furthermore, the control unit 52 receives information about the flow, i.e. the volume per unit of time of molten metal through the shroud. This piece of information is received over a flow input line 58 which at its other end is connected to a flow determining device (not shown), which can be either a direct measuring device or an indirect measuring device with subsequent calculation, as previously explained. If it is determined that a significant change in flow of molten metal has occurred, the control unit 52 will set a different voltage range. A decreased flow results in the setting of a larger voltage range and an increased flow results in the setting of a narrower voltage range. Thus, the point at which the alarm unit 54 is activated is dependent on the received flow information.

Figure 2:
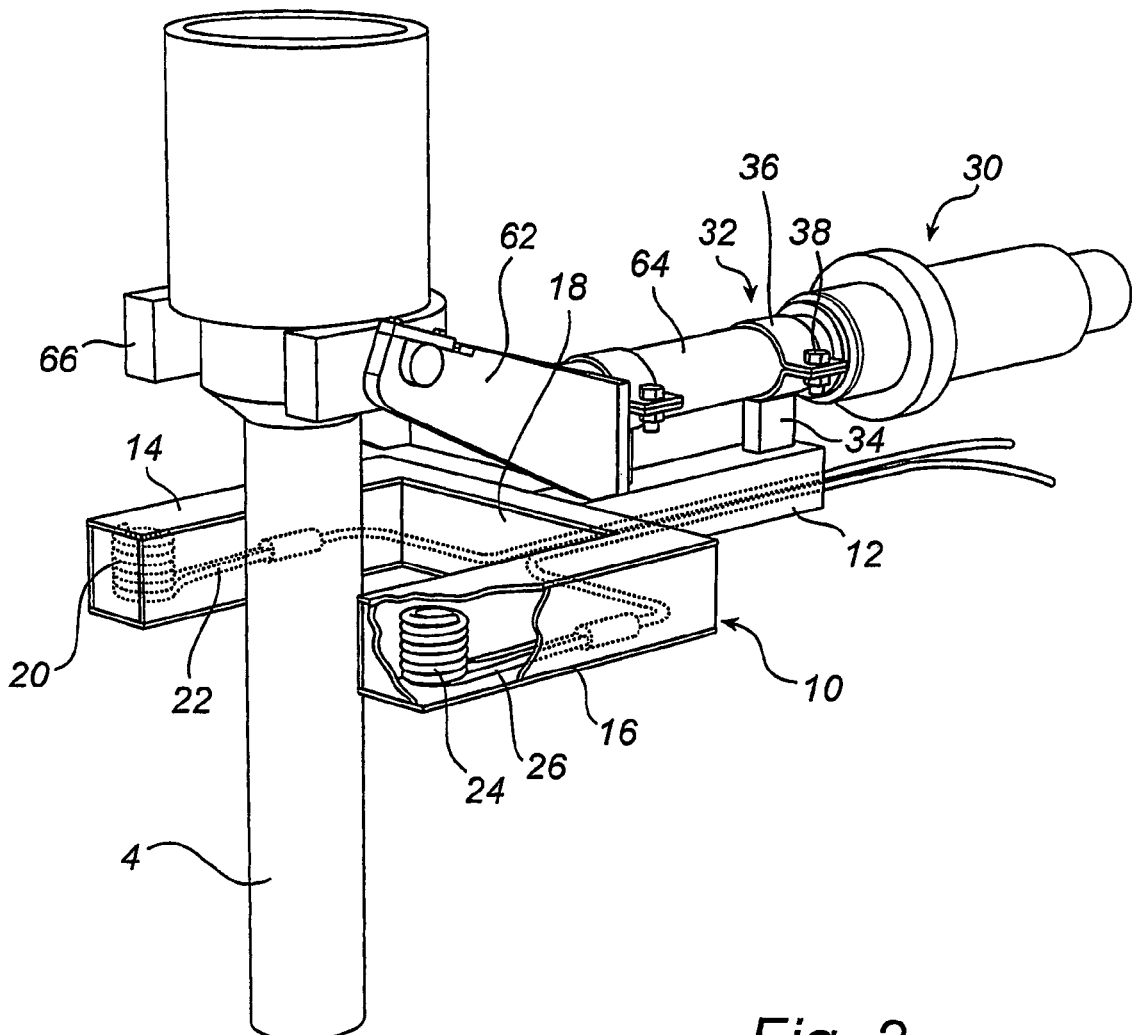
FIG. 2 is a more detailed schematic illustration of the components shown around the shroud in FIG. 1.

In FIG. 2 the forked coil holder 10 and its suspension to the shroud manipulator 30 holding the shroud 4 is shown in more detail. FIG. 2 is a partly cut away perspective view. The forked coil holder 10 comprises a stem portion 12, a first branch portion 14, a second branch portion 16 and a cross bar portion 18. In this embodiment the branch portions 14, 16 are located at opposite ends of the cross bar portion 18 and the stem portion 12 is connected to the middle of the cross bar portion 18. However, in alternative embodiments the stem portion could be placed at one end of the cross bar portion and even be an elongation of one of the branch portions.

FIG. 2 illustrates that the interior of the first branch portion 14 comprises at its end farthest from the cross bar portion 18 a transmitting coil 20. The wires 22 of the transmitting coil are passed through the first branch portion 14, via the cross bar portion 18 and the base portion 12 to the control unit (see also FIG. 1).

FIG. 2 also illustrates that the interior of the second branch portion 16 comprises at its end farthest from the cross bar portion 18 a receiving coil 24. The wires 26 of the receiving coil 24 are passed through the second branch portion 16, via the cross bar portion 18 and the base portion 12 to the control unit (see also FIG. 1).

The ends of the branches portions 14, 16 are so positioned that the transmitting coil 20, the shroud 4 and the receiving coil 24 are located in a straight line. In other words, the shroud 4 is located between the two coils 20, 24. The branch portions 14, 16, or sections thereof, may be controllable between different angles relative to the rest of the forked coil holder. This enables the coils 20, 24 to be correctly positioned for setting the main direction of propagation of the electromagnetic field at a right angle to the shroud in working position.

The wires of the two coils 20, 24 may be electrically isolated from one another in the cross bar portion 18 and the stem portion 12 in order to avoid unwanted electromagnetic influence on any signals.

The forked coil holder 10 is suitably made of mainly non-magnetic material, such as any one of stainless steel, ceramic material, fibre glass or other similar suitable material that substantially does not interfere with the electromagnetic field.

The forked coil holder 10 is suspended to the shroud manipulator 30 by means of a clamping arrangement 32 comprising two protrusions 34 each of them having at its end a clamp 36 surrounding the shroud manipulator 30. The clamps 36 are tightened to the shroud manipulator 30 by means of bolts or screws 38.

The shroud manipulator 30 illustrated in FIG. 2 is of standard type and comprises at the end portion that holds the shroud 4 a gripping means. The gripping means comprises two grip portions 62 that are inclined upwards from the rear elongate portion 64 of the shroud manipulator 30. The inclination depends among other things on how the shroud is to be positioned. The initial gripping point on the shroud differ from the shroud positioning point of the manipulator, making it desirable to change the angle. The grip portions 62 are further connected to a holder 66 shaped as a horse shoe.

Figure 3:
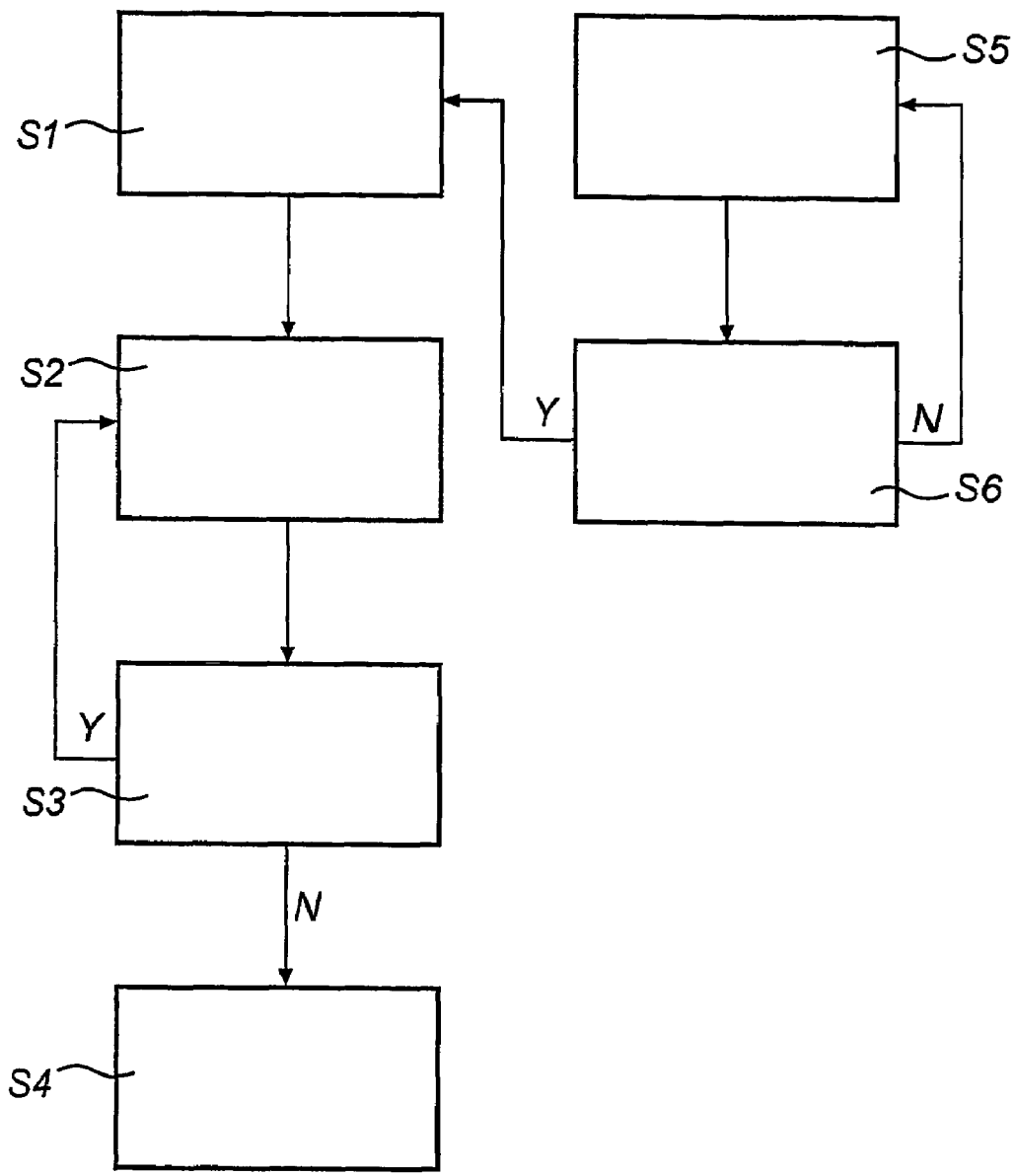
FIG. 3 is a flow chart illustrating an example of an operation of a control unit.

FIG. 3 is a flow chart illustrating an example of an operation of the control unit 52 shown in FIG. 1.

In a step S1 the control unit defines a voltage range. In a step S2 the control unit receives a signal indicative of the voltage induced at the receiving coil. In a step S3 the control unit compares the value of the received signal with the defined voltage range and determines whether or not said value is within the defined voltage range. If said value is not within the defined voltage range (in such a case the absolute value of the received signal is generally larger then the absolute value of the maximum voltage of the voltage range), then the control unit activates a slag detection alarm in a step S4. If on the other hand it is determined in step S3 that the value of the received signal is encompassed by the defined voltage range, the control unit returns to step S2 to receive a new signal to be compared in the subsequent step S3 etc.

In parallel to said steps, the control unit also receives a flow signal in a step S5. The flow signal is indicative of the volume per unit of time of molten metal flowing through the shroud. In a step S6 the control unit compares the determined flow of molten metal with stored values and examines whether or not there has been a significant change of flow over time. If there has been no significant change the control unit continues with the step S5 to examine subsequent flow signals. However, if there is a significant change, the control unit will in accordance with the stored values (such as a table) redefine the voltage range in the step S1.

It should be noted that FIG. 3 is only an example of the operation of the control unit for elucidating purposes and that other alternatives are also possible.

It should also be noted that numerous modifications and variations can be made without departing from the scope of the present invention defined in the accompanied claims. For instance, even though the description is focused on the use of one transmitting coil and one receiving coil, the method and device according to the invention may comprise several transmitting coils and several receiving coils.

The invention claimed is:

1. A method of detecting the presence of slag in a shroud for guiding molten metal from a ladle to a tundish, the method comprising:

generating, by means of at least one transmitting coil, an electromagnetic field that enters the shroud and its contents;

generating an induced voltage by means of at least one receiving coil which is subjected to the electromagnetic field having entered the shroud and its contents, wherein any induced voltage having a value outside a defined voltage range is indicative of the presence of slag in said contents;

determining the flow of the molten metal passing through the shroud; and defining said voltage range depending on the magnitude of the determined flow of molten metal.

2. The method as claimed in claim 1, further comprising:
keeping the coils substantially unmovable relative to the shroud.

3. The method as claimed in claim 1, further comprising:
providing a forked coil holder having at least two branches;
mounting the transmitting coil to a first branch and the receiving coil to a second branch of the forked coil holder; and
placing the forked coil holder in such manner that an imagined straight line drawn between the transmitting coil and the receiving coil crosses the shroud.

4. The method as claimed in claim 3, wherein the act of placing the forked coil holder comprises mounting said forked coil holder to a shroud manipulator.

5. The method as claimed in claim 3, wherein the act of placing the forked coil holder comprises mounting said forked coil holder to a separate mounting device that is arranged to follow the position of the shroud.

6. The method as claimed in claim 3, wherein the act of placing the forked coil holder comprises mounting said forked coil holder to a sliding gate at the ladle.

7. The method as claimed in claim 1, further comprising:
providing said at least one transmitting coil in toroid form and arranging it so as to surround the shroud, and
providing said at least one receiving coil in toroid form and arranging it so as to surround the shroud.

8. The method as claimed in claim 1, further comprising:
detecting turbulent flow, if any, inside the shroud; and
changing the frequency of the electromagnetic field generated by the transmitting coil in case of turbulent flow having been detected.

9. The method as claimed in claim 1, further comprising generating, by means of said at least one transmitting coil:
an electromagnetic field of alternating frequencies, or
several electromagnetic fields with different frequencies.

10. The method as claimed in claim 1, further comprising:
defining a larger voltage range if it is determined that the magnitude of the flow of molten metal has decreased.

11. The method as claimed in claim 1, wherein the act of determining the flow of molten metal passing through the shroud comprises:
providing feedback from an opening position signal of a sliding gate at the ladle and calculating the flow of molten metal from the sliding gate opening information.

12. The method as claimed in claim 1, wherein the act of determining the flow of molten metal passing through the shroud comprises:
measuring the rate of decrease in weight of the ladle content and calculating the flow of molten metal from said measured rate of decrease in weight.

13. The method as claimed in claim 1, wherein the act of determining the flow of molten metal passing through the shroud comprises:

measuring the teeming rate in the tundish and calculating the flow of molten metal from said measured teeming rate.

14. The method as claimed in claim 1, further comprising: cooling said transmitting and receiving coils.

15. A device for detecting the presence of slag in a shroud for guiding molten metal from a ladle to a tundish, comprising:
   at least one transmitting coil for generating an electromagnetic field to be entered into the shroud and its contents;
   at least one receiving coil for receiving the electromagnetic field that has entered the shroud and its contents, and for generating an induced voltage, wherein any induced voltage having a value outside a defined voltage range is indicative of the presence of slag in said contents;
   means for determining the flow of the molten metal passing through the shroud; and
   means for defining said voltage range depending on the magnitude of the measured flow.

16. The device as claimed in claim 15, further comprising a coil holder arrangement which is mountable in such manner that the coils are enabled to substantially follow positional variations of the shroud.

17. A device as claimed in claim 16, wherein said coil holder arrangement comprises a forked coil holder having at least two branches, a first branch carrying the at least one transmitting coil and a second branch carrying the at least one receiving coil, the two branches being placeable in such manner that the shroud is located between them.

18. The device as claimed in claim 17, wherein the forked coil holder is adapted to be mounted to a shroud manipulator.

19. The device as claimed in claim 17, wherein the forked coil holder is adapted to be mounted to a separate mounting device which is arranged to follow the position of the shroud.

20. The device as claimed in claim 17, wherein the forked coil holder is adapted to be mounted to a sliding gate at the ladle.

21. The device as claimed in claim 17, wherein said two branches are electrically isolated from each other.

22. The device as claimed in claim 15, wherein said coils are in the form of toroids, wherein said coil holder arrangement is adapted to hold each toroid in such manner that it surrounds the shroud.

23. The device as claimed in claim 15, wherein said means for determining the flow of the molten metal passing through the shroud comprises:
   a sensor for sensing an opening position signal of a sliding gate at the ladle, and
   a processor for calculating the flow of molten metal from the sliding gate opening information.

24. The device as claimed in claim 15, wherein said means for determining the flow of the molten metal passing through the shroud comprises:
   a measuring device for measuring the rate of decrease in weight of the ladle content, and
   a processor for calculating the flow of molten metal from said measured rate of decrease in weight.

25. The device as claimed in claim 15, wherein said means for determining the flow of the molten metal passing through the shroud comprises:
   a measuring device for measuring the teeming rate in the tundish, and
   a processor for calculating the flow of molten metal from said measured teeming rate.

26. The device as claimed in claim 15, wherein the transmitting and receiving coils are provided with directional elements, such as a core, for directing the electromagnetic field towards and from the shroud.

27. A device as claimed in claim 15, further comprising a casting plant, the casting plant including:
   a ladle adapted to contain molten metal;
   a tundish adapted to receive molten metal from the ladle;
   a shroud arranged between the ladle and the tundish, wherein molten metal is enabled to pass from the ladle, through the shroud, and to the tundish.

* * * * *